United States Patent [19]

Carruthers

[11] 3,934,914
[45] Jan. 27, 1976

[54] DEVICE FOR INSERTING AND REMOVING CONTACT LENS

[76] Inventor: Eben H. Carruthers, P.O. Box 40, Warrenton, Oreg. 97146

[22] Filed: July 11, 1974

[21] Appl. No.: 487,729

[52] U.S. Cl............................. 294/1 CA; 294/64 R
[51] Int. Cl.² ......................................... A61F 9/00
[58] Field of Search ........ 294/1 CA, 64 R; 128/303; 351/160

[56] References Cited
UNITED STATES PATENTS
2,384,334  9/1945  Olson ...................... 294/1 CA UX
3,129,971  4/1964  Kobler ......................... 294/1 CA X
3,791,689  2/1974  Boone et al. .................... 294/1 CA FOREIGN PATENTS OR APPLICATIONS
267,965   7/1970  U.S.S.R. ........................... 294/1 CA
1,255,345 11/1967  Germany .......................... 294/1 CA Primary Examiner—Evon C. Blunk
Assistant Examiner—Johnny D. Cherry
Attorney, Agent, or Firm—Kolisch, Hartwell, Dickinson & Stuart

[57] ABSTRACT

A device for aid in inserting or removing a contact lens including an elongate, resilient, cylindrical tube having a contact lens holding cup formed at one end thereof communicating with the interior of the tube. A light transmitting closure member is press fit in the opposite end of the tube to provide an airtight closure at that end of the tube. Opposite sides of a resilient portion of the tube are manually flexible toward and away from each other to evacuate a portion of the tube and, upon release and with a contact lens seated on the lens holding cup, return to their original configuration to produce a subatmospheric pressure within the tube to hold the lens on the lens holding cup. An elongate, light transmitting, manually incompressible shaft extends longitudinally through the interior of the tube to prevent opposed sides of the tube from being squeezed completely together, thus to provide a light transmitting path between the closure at one end and the lens holding cup at the other end to aid in sighting through the device during operation.

7 Claims, 7 Drawing Figures

DEVICE FOR INSERTING AND REMOVING CONTACT LENS

BACKGROUND AND SUMMARY OF THE INVENTION

This invention relates to a device for aid in inserting and removing a contact lens, and more particularly, to a device which maintains a light transmitting path therethrough along which path a user may sight during operation.

Various devices have been designed in the past for aiding contact lens wearers to insert and remove contact lenses. Included in such prior devices are those which use a squeeze bulb type holder having a lens receiving cup at one end thereof, with resilient sides which may be manually squeezed together and released to provide a subatmospheric pressure within the bulb to hold the contact lens on the cup. For the most part, such prior devices have had no provision for providing a light transmitting path through the device along which the user may sight to maintain his eye in a desired orientation while operating the device. Those which may have had some provision for sighting have not been of such design so as to be able to maintain a light transmitting path through the device on pressing of opposed sides of the bulb together to evacuate the bulb.

A general object of the present invention is to provide a simple and economically constructed device for aid in inserting and removing contact lenses which overcomes the above set-out objections of prior art devices in a simple and effective manner.

More specifically, an object is to provide a novel device for inserting and removing contact lenses which includes an elongate, hollow tube having a lens holding portion at one of its ends and a light transmitting closure at the other end, with the interior of the device providing a light transmitting path from the lens holding portion to the closure. Opposite sides of an intermediate portion of the tube are flexible toward and away from each other to evacuate a portion of the interior of the tube to produce a subatmospheric pressure for holding a contact lens on the lens holding portion. An elongate, light transmitting shaft extends longitudinally through the intermediate flexible portion to prevent the opposite sides of the tube from being squeezed tightly together, and thus maintains a light transmitting path through the device along which the user may sight throughout operation.

DRAWINGS

These and other objects and advantages will become more fully apparent as the following description is read in conjunction with the drawings, wherein.

Figure 1:
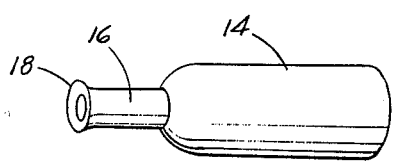
FIG. 1 is a perspective view of a resilient, cylindrical main body for a device constructed according to an embodiment of the invention.
Figure 2:
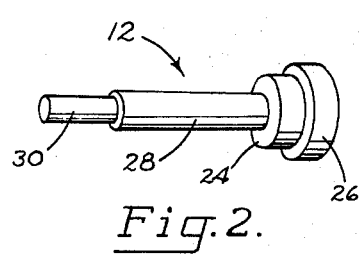
FIG. 2 is a perspective view of a combination closure element and light transmitting shaft which is insertable into the body illustrated in FIG. 1.
Figure 3:
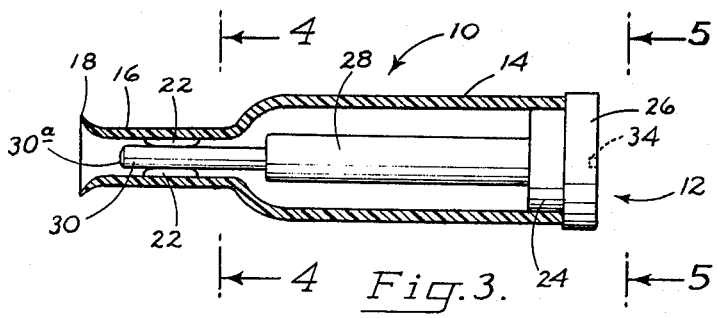
FIG. 3 is an enlarged longitudinal cross section of the device with the body, closure element, and shaft assembled in operative position.
Figure 4:
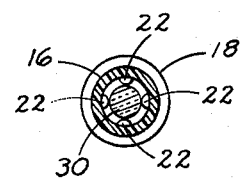
Figure 6:
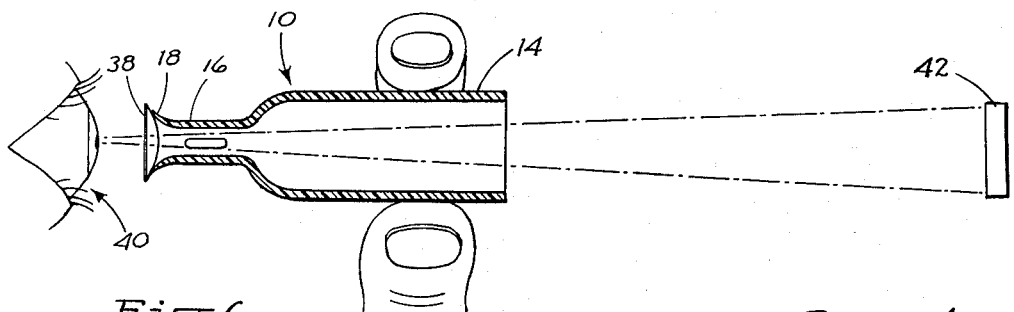
Figure 5:
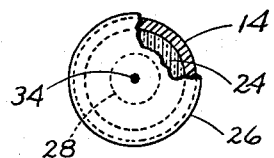
Figure 7:
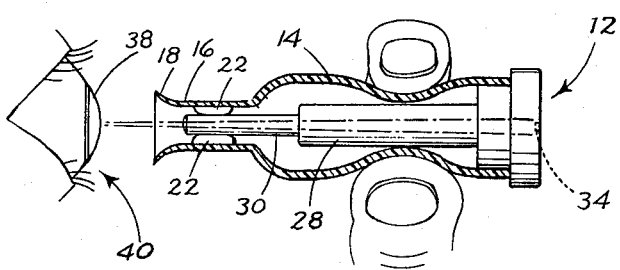

FIGS. 4 and 5 are views taken generally along the lines 4—4 and 5—5, respectively, in FIG. 3, with portions broken away in FIG. 5;

FIG. 6 is a longitudinal cross-sectional view, on a smaller scale than shown in FIG. 3, of the device as it may be used for inserting a contact lens; and FIG. 7 is a longitudinal cross-sectional view of the device in operative position just prior to removal of the contact lens.

DETAIL DESCRIPTION OF A PREFERRED EMBODIMENT OF THE INVENTION

Referring to the drawings, the device of the invention includes a main body portion indicated generally at 10 and a combination closure and light transmitting member indicated generally at 12. Body 10 is an elongate hollow tube, formed in the generally bottle-shaped configuration illustrated of rubber or a plastic with resilient, rubber-like properties. A material which has been found to work well is silicon rubber having a durometer hardness of about 50–60. The body includes an elongate, hollow, cylindrical major body portion 14, also referred to as a resilient portion, which, with member 12 removed is open at its right end. An elongate, hollow, cylindrical, smaller diameter neck, or intermediate, portion 16 extends longitudinally outwardly from the left end of portion 14 and a flaring mouth, or contact lens receiving and holding, portion 18 projects outwardly from the left end of neck portion 16, as illustrated in the figures. The outer diameter of mouth portion 18 is less than the diameter of a contact lens.

As is seen in FIGS. 3 through 7, the internal diameter, or side-to-side dimension between opposed sides, in main body portion 14 is greater than the internal diameter, side-to-side dimension, in neck portion 16. A plurality of spacer members 22 spaced circumferentially about the inside of neck portion 16 project radially inwardly therefrom.

Member 12 is formed of a substantially rigid, manually incompressible, light transmitting material such as clear acrylic plastic. As seen in the figures, member 12 includes a closure portion consisting of a cylindrical sealing section, or portion, 24 and a larger diameter limiting section, or portion, 26. Sealing section 24 is of such diameter that it may be inserted into the open end of main body portion 14 of member 10, providing a press fit therein to produce an airtight seal between sealing section 24 and main body portion 14. The limiting section 26, being of greater diameter than section 24 abuts the end of the main body portion, upon insertion of the sealing section, to limit insertion to a preselected position.

An elongate, cylindrical shaft portion, or section, 28 projects outwardly from the center of sealing section 24. Shaft portion 28 has a diameter which is smaller than the internal diameter of resilient portion 14 and has a length less than the length of resilient portion 14, whereby it terminates short of the end of portion 14. An elongate, cylindrical stem portion, or section, 30 projects longitudinally outwardly from the end of shaft portion 28. Stem portion 30 has such length that when the parts are assembled, as illustrated in FIGS. 3 through 7, it extends through part of neck portion 16 but terminates in a region spaced inwardly from mouth portion 18. Its outer end extremity 30a may be optically ground to a convex configuration. The diameter of stem portion 30 is slightly less than the internal diameter of neck portion 16 and is such as to fit tightly between the inwardly facing surfaces of spacer members 22.

A small, opaque dot 34 is imprinted centrally on the end of limiting portion 26 of member 12. This dot is to act as a sighting indicia to assist in aligning the device with a user's eye, as will be explained in greater detail below.

Explaining the operation of the device, reference first is made to FIG. 6 which illustrates how the device may be used to apply a contact lens 38 to a user's eye 40. For the insertion of a contact lens, body 10 may be used alone. The lens first is coated with a liquid cushioning, or wetting, solution of a type generally used with contact lenses. The lens then is placed centrally in the flared opening of mouth portion 18 with the convex side of the lens in the mouth portion. The lens is held in position on the flared mouth portion by the tension of the liquid alone.

Body 10 is held lightly, as shown in FIG. 6 whereby the sides of the body portion 14 are not depressed, and the tube and lens are brought into position adjacent the eye as illustrated. As the lens near the eye a line of sight may be maintained through the lens and the tube, with the user sighting at a small object, such as a lens case indicated generally at 42 which may be resting on a counter in the region of use. As the contact lens is moved closer to the eye, the tubular body and lens may be adjusted laterally and angularly to keep the appearance of the sighted object centrally in the open end of the tube. The lens thus makes initial contact close to the central portion of the eye. The tube then is withdrawn from the eye leaving the lens of the eye.

Although operation of the device for inserting a contact lens has been described using tubular body 10 alone, it should be realized that it may be used with body 10 and member 12 assembled as shown in FIG. 3 also for inserting a lens.

Explaining a use of the device for removal of a contact lens, and referring to FIGS. 3 and 7, body 10 and member 12 first are assembled as illustrated. When thus assembled sealing portion 24 of member 12 provides an airtight seal at one end of the main body, and shaft and stem portions 28, 30 extend longitudinally through the tubular body. Stem portion 30 fits snugly against the radially inwardly facing surfaces of spacers 22 with the spaces between spacers 22 providing air flow passages extending from mouth portion 18 into the interior of main body portion 14.

Referring to FIG. 7, with members 10, 12 assembled as described, the sides of main body portion 14 are manually squeezed toward each other as illustrated to evacuate a portion of the interior of the tube. The user then directs the device toward contact lens 38 which is to be removed from eye 40 and sights directly through the tubular body and member 12 to align the device properly with his eye. The light transmitting characteristics of the closure and light transmitting member 12 allow the user to look directly through the shaft and stem portions 28, 30 to sight on opaque dot 34 at the end of the tube. The convex configuration of end extremity 30a of the stem portion of the device provides a degree of magnification which assists in maintaining proper alignment by magnifying dot 34 to aid in aligning it in the device. As the device is brought near the eye the position of the tube may be adjusted laterally and angularly so that dot 34 appears centrally in the lighted end area of the tube. When so positioned, the assembly is properly aligned to contact and remove the contact lens.

It should be noted that shaft portion 28 prevents the sides of the tube from being squeezed completely together, thus to maintain a path along which light is transmitted from one end of the device to the other for sighting and aligning purposes.

When mouth portion 18 of the device touches the contact lens, finger pressure is relaxed to allow the tube's side walls to return to their initial configuration as illustrated in FIG. 3. This produces a subatmospheric pressure within the tube providing a partial vacuum to hold the contact lens to the mouth portion of the device. The device then is withdrawn from the eye, taking the contact lens with it.

In such a device, the shaft and stem portions of member 12 have two-fold purpose. First, they maintain a light path through the cylinder when the walls of the cylinder are pressed inwardly as shown in FIG. 7, and secondly, they provide a degree of stiffness for the device to aid in assuring alignment of neck portion 16 with a line of sight through the device.

An added advantage of such a device, in which the body portion 10 and member 12 are disassembleable, is that the same lends itself to simple and effective cleansing. This is particularly important when dealing with contact lenses and working around the eyes.

While a preferred embodiment of the invention has been described herein, it should be apparent to those skilled in the art that variations and modifications are possible without departing from the spirit of the invention.

It is claimed and desired to secure by Letters Patent:

1. A device for use in inserting and removing a contact lens comprising:
    an elongate, hollow tube having a lens holding portion at one end thereof opening into the interior of said tube and a portion of said tube spaced from said one end being resilient to accommodate manual flexing of opposed sides thereof toward each other and to return substantially to their original configuration when released,
    a light transmitting closure element attached to and providing an airtight closure of the other end of said tube, and
    an elongate, substantially rigid, straight light transmitting shaft of smaller side-to-side dimension than the interior of said resilient portion of the tube secured at one of its ends to said closure element and extending axially of said tube through the resilient portion of said tube, with its other end adjacent but spaced inwardly from said lens holding portion of the tube, said shaft being operable to prevent said opposed sides of the tube from being pressed into contact with each other, thus to maintain a line of sight light path extending axially of said tube from said closure element to said lens holding portion during flexing of said tube walls toward each other.

2. The device of claim 1, which further comprises spacer means interposed between the inner surface of said tube and said shaft adjacent said lens holding portion, said spacer means being operable to maintain an air flow passage extending between said lens holding and resilient portions of the tube.

3. The device of claim 1, wherein said shaft is constructed of a material which is manually incompressible.

4. The device of claim 1, wherein a portion of the tube intermediate said resilient portion and said lens holding portion has an interior surface of a side-to-side dimension less than the internal side-to-side dimension of said resilient portion, and a section of said shaft extending into said intermediate portion of the tube is of a side-to-side dimension less than said dimension of said intermediate portion to provide an air flow passage between said lens holding and resilient portions of the tube.

5. The device of claim 1, wherein said closure member has sighting indicia inscribed thereon.

6. The device of claim 5, wherein the end extremity of said shaft adjacent said lens holding portion is convex.

7. The device of claim 1, wherein said closure element and shaft are removably mounted in said tube.

* * * * *